US010251604B2

(12) United States Patent
Coleman et al.

(10) Patent No.: US 10,251,604 B2
(45) Date of Patent: Apr. 9, 2019

(54) SENSITIVE, HIGH-STRAIN, HIGH-RATE, BODILY MOTION SENSORS BASED ON CONDUCTIVE NANO-MATERIAL-RUBBER COMPOSITES

(71) Applicant: The Provost, Fellows, Foundation Scholars, And The Other Members Of Board, Of The College Of The Holy And Undivided Trinity Of Queen Elizabeth, Near Dublin, Dublin (IE)

(72) Inventors: Jonathan Coleman, Dublin (IE); Conor Boland, Clontarf (IE); Umar Khan, Dublin (IE)

(73) Assignee: The Provost, Fellows, Foundation Scholars, and the other Members of Board, of the College of the Holy and Undivided Trinity of Queen Elizabeth, near Dublin, Dublin (IE)

( * ) Notice: Subject to any disclaimer, the term of this patent is extended or adjusted under 35 U.S.C. 154(b) by 122 days.

(21) Appl. No.: 15/026,888

(22) PCT Filed: Mar. 14, 2014

(86) PCT No.: PCT/EP2014/055184
§ 371 (c)(1),
(2) Date: Apr. 1, 2016

(87) PCT Pub. No.: WO2015/049067
PCT Pub. Date: Apr. 9, 2015

(65) Prior Publication Data
US 2016/0287175 A1    Oct. 6, 2016

Related U.S. Application Data

(60) Provisional application No. 61/885,927, filed on Oct. 2, 2013.

(51) Int. Cl.
| | |
|---|---|
| C08L 9/00 | (2006.01) |
| A61B 5/00 | (2006.01) |
| C08J 3/21 | (2006.01) |
| C08J 3/215 | (2006.01) |
| A61B 5/024 | (2006.01) |
| A61B 5/113 | (2006.01) |
| C08K 3/01 | (2018.01) |
| A61B 5/08 | (2006.01) |
| B82Y 30/00 | (2011.01) |

(52) U.S. Cl.
CPC ........ *A61B 5/6831* (2013.01); *A61B 5/02438* (2013.01); *A61B 5/02444* (2013.01); *A61B 5/1135* (2013.01); *A61B 5/6823* (2013.01); *C08J 3/212* (2013.01); *C08J 3/215* (2013.01); *C08K 3/01* (2018.01); *C08L 9/00* (2013.01); *A61B 5/0816* (2013.01); *A61B 5/6824* (2013.01); *A61B 2562/0266* (2013.01); *A61B 2562/0285* (2013.01); *A61B 2562/12* (2013.01); *B82Y 30/00* (2013.01); *C08J 2307/00* (2013.01); *C08K 2201/001* (2013.01); *C08K 2201/011* (2013.01)

(58) Field of Classification Search
CPC ......... C08J 3/215; C08J 3/212; C08K 3/0008; C08K 3/01; C08L 9/00
See application file for complete search history.

(56) References Cited

U.S. PATENT DOCUMENTS

| | | |
|---|---|---|
| 2006/0292033 A1 | 12/2006 | Blok et al. |
| 2012/0266685 A1 | 10/2012 | Choi et al. |
| 2013/0149772 A1 | 6/2013 | Lee et al. |

FOREIGN PATENT DOCUMENTS

| | | |
|---|---|---|
| GB | 701 156 | 12/1953 |
| GB | 929 152 | 6/1963 |
| WO | WO 2007/010517 | 1/2007 |

OTHER PUBLICATIONS

International Search Report, for International Appl. No. PCT/EP2014/055184, dated Feb. 6, 2015, consisting of 6 pages, entitled "Sensitive, High-Strain, High-Rate, Bodily Motion Sensors Based on Conductive Nano-Material-Rubber Composites."

*Primary Examiner* — Hannah J Pak
(74) *Attorney, Agent, or Firm* — Hamilton, Brook, Smith & Reynolds, P.C.

(57) ABSTRACT

A process for producing conductive composites, the process comprising the steps of soaking a polymer in an organic solvent and applying energy; soaking the polymer in a solution of conductive nano-material dispersed in an organic solvent:water mixture and applying energy, so that conductive nano-material is incorporated into the polymer structure; washing the conductive nano-material-incorporated polymer in deionized water and applying energy; and drying the washed conductive nano-material-incorporated polymer to produce the conductive composite, wherein the conductive composite incorporates conductive nano-material throughout the structure of the polymer without affecting the integrity of the properties of the polymer.

14 Claims, 5 Drawing Sheets

SENSITIVE, HIGH-STRAIN, HIGH-RATE, BODILY MOTION SENSORS BASED ON CONDUCTIVE NANO-MATERIAL-RUBBER COMPOSITES

This application is the U.S. National Stage of International Application No. PCT/EP2014/055184, filed Mar. 14, 2014, which designates the U.S., published in English, and claims the benefit of U.S. Provisional Application No. 61/885,927, filed Oct. 2, 2013. The entire teachings of the above applications are incorporated herein by reference.

FIELD OF THE INVENTION

The invention relates to the field of sensors such as biosensors. More particularly, the invention relates to the integration of electronics with biological or other soft, stretchable, flexible systems for use as sensors.

BACKGROUND TO THE INVENTION

The past decade has seen a growing body of research devoted to the integration of electronics with biological or other soft, stretchable, flexible systems. This field is broad, ranging from wearable bio-sensors to ultra-light, foldable plastic electronics. An important sub-field involves the development of devices or sensors to be mounted on or near the skin. Clearly, because of the soft, compliant nature of tissue and the natural bending or rotational motion associated with joints, many applications in this area will require the development of both structures and materials which can stretch, bend, fold, twist and generally deform in response to the motion of the wearer. Such behaviour is generally not compatible with traditional silicon based electronics. This has led to the development of various stretchable materials and structures which have been used to fabricate a range of other devices including transistors and sensors which can be integrated into clothing or worn on the skin.

A particularly important class of stretchable electronics encompasses wearable biosensors which can be fabricated to monitor a range of bio-signals including blood pressure, respiration rate and blood glucose levels. Particularly important are wearable strain and motion sensors. These can be used to monitor joint and muscle motion and can be used for sensing of posture, movement and even breathing. A number of applications have been suggested for such sensors: smart suits for babies, athletes or soldiers or in monitoring of patients which are elderly, suffer from chronic disease or are in rehabilitation.

Such strain and motion sensors usually work by sensing the change in resistance of a material in response to variations in its length. However, wearable strain sensors have a range of requirements that are not all fulfilled by standard strain sensing platforms. Such sensors need to be compliant so as not to limit the motion of the wearer; they need to be highly sensitive to detect small motions involved in processes such as breathing; they need to work at high strains to monitor large scale motion such as that associated with joints and finally, need to operate at high speeds/strain rates to follow fast voluntary and involuntary movement. In addition, it should be possible to produce the sensing material in various shapes, sizes and geometries, for example as fibres which could be woven into garments. It should also be cheap to produce to facilitate widespread availability. To the authors knowledge no material combines all these properties, severely limiting our ability to fabricate multifunctional wearable strain and motion sensors.

This is unfortunate as sensors made from such materials could sense not only strain but velocity, acceleration and force. Such capabilities would facilitate not only applications in human motion sensing but in a range of areas including monitoring of airbags and other inflatable devices, motion in robots or moving mechanical objects and vibration monitoring.

In order to develop materials which can perform this array of functions, many researchers have turned to materials science and specifically nanotechnology. Strain sensors have been demonstrated from a range of materials and structures including hydrogels, nano-papers, graphene woven fabrics, nanotube arrays and complex nano-engineered structures. Particularly promising have been the nano-composite strain gauges. To date, strain gauges prepared from polymer-nanoparticle composies, polymer nanotube composites, polymer-graphene composites and polymer-carbon black composites have demonstrated performance far superior than those observed for commercial metal stain gauges.

The simplest performance metric is the gauge factor, G, which describes how the relative resistance change depends on strain, $\varepsilon$: $\Delta R/R_0 = G\varepsilon$. This is usually measured at low strain and is typically ~2 for metal strain gauges. However, some nano-composites have demonstrated values of G as high as 30. Some results have been extremely impressive. Networks of graphene on elastomeric substrates have demonstrated high gauge factor and good dynamic performance at strains up to 8%. By fabricating arrays of platinum coated polymer nanofibers. Low-strain sensors for pressure, shear and torsion with good dynamic response up to 10 Hz have previously been fabricated. Arrays of carbon nanotubes have also been used to prepare high-strain sensors with very impressive dynamic response but relatively low gauge factor. However, no reports exist for strain sensors which combine low stiffness, high gauge factor, high-strain and fast dynamic motion sensing capabilities with the potential for simple, cheap fabrication.

It is an object of the subject application to overcome at least one of the above-mentioned problems.

SUMMARY OF THE INVENTION

The present invention provides a very simple method to infiltrate store-bought elastic bands with liquid-exfoliated graphene or other conductive nano-materials to produce versatile strain sensors. The simple strain sensors of the present invention work very well at strains of up to 600%, both under quasi-static conditions or at dynamic strain rates of at least 7000%/s. In addition, the sensors of the invention have been demonstrated to have impressive performances when used as kinesthetic motion sensors, detecting motions as subtle as those associated with breathing and pulse. The performance is consistent and repeatable over many cycles.

According to the invention, there is provided a process for producing conductive composites, the process comprising the steps of:

(a) soaking a polymer in an organic solvent and applying energy;

(b) soaking the polymer in a solution of conductive nano-material dispersed in an organic solvent:water mixture and applying energy, such that the conductive nano-material is incorporated into the polymer structure;

(c) washing the conductive nano-material-incorporated polymer in deionised water and applying energy; and (d) drying the washed conductive nano-material-incorporated polymer to produce the conductive composite, wherein the conductive composite incorporates the nano-material throughout the structure of the polymer without affecting the integrity of the properties of the polymer.

According to the invention, there is provided, as set out in the appended claims, a process for producing conductive composites, the process comprising the steps of:
(a) soaking a polymer in an organic solvent;
(b) soaking the polymer in a solution of conductive nano-material dispersed in an organic solvent:water mixture, such that the conductive nano-material is incorporated into the polymer structure;
(c) washing the conductive nano-material-incorporated polymer in deionised water; and
(d) drying the washed conductive nano-material-incorporated polymer to produce the conductive composite, wherein the conductive composite incorporates the nano-material throughout the structure of the polymer without affecting the integrity of the properties of the polymer.

According to the invention, there is provided a process for producing conductive composites, the process comprising the steps of:
a) soaking a polymer in an aqueous surfactant solution and applying energy;
b) soaking the polymer in a solution of conductive nano-material dispersed in an aqueous surfactant solution and applying energy, such that the conductive nano-material is incorporated into the polymer structure;
c) washing the conductive nano-material-incorporated polymer in deionised water and applying energy; and
d) drying the washed conductive nano-material-incorporated polymer to produce the conductive composite, wherein the conductive composite incorporates the nano-material throughout the structure of the polymer without affecting the integrity of the properties of the polymer.

According to the invention, there is provided, as set out in the appended claims, a process for producing conductive composites, the process comprising the steps of:
(a) soaking a polymer in an aqueous surfactant solution;
(b) soaking the polymer in a solution of conductive nano-material dispersed in an aqueous surfactant solution, such that the conductive nano-material is incorporated into the polymer structure;
(c) washing the conductive nano-material-incorporated polymer in deionised water; and
(d) drying the washed conductive nano-material-incorporated polymer to produce the conductive composite, wherein the conductive composite incorporates the nano-material throughout the structure of the polymer without affecting the integrity of the properties of the polymer.

The term "nano-material" should be understood to mean any conductive exfoliated 2-dimensional material or 1-dimensional material suitable for incorporation into a polymer.

In one embodiment, the conductive nano-material is an exfoliated 2-dimensional material obtained from exfoliating any suitable 3-dimensional layered compound, for example graphite.

In one embodiment, the conductive nano-material is an exfoliated 2-dimensional material obtained from exfoliating any suitable 3-dimensional layered compound, for example any transition metal dichalcogenide having the formula $MX_n$, or any other layered material such as transition metal oxides, boron nitride (BN), $Bi_2Te_3$, $Sb_2Te_3$, TiNCl, $MoO_3$ or any other inorganic layered compound. When the 3-dimensional transition metal dichalcogenide has the formula $MX_n$, M may be selected from the group comprising Ti, Zr, Hf, V, Nb, Ta, Cr, Mn, Mo, W, Tc, Re, Ni, Pd, Pt, Fe, and Ru; X may be selected from the group comprising O, S, Se, and Te; and $1 \leq n \leq 3$, for example, $VS_2$, $NbSe_2$ or $TaS_2$.

In one embodiment, the conductive nano-material is a 1-dimensional material selected from the group comprising carbon nanotubes, silver nanowires, platinum nanowires, gold nanowires, palladium nanowires, or any metallic nanowire.

In one embodiment, the conductive nano-material is the exfoliated 2-dimensional material graphene.

In one embodiment of the invention, the exfoliated graphene used in the process of the present invention may be used for the mechanical reinforcement of polymers, to reduce the permeability of polymers, to enhance the conductivity (electrical and thermal) of polymers, and to produce conductors and electrode materials.

In one embodiment, the process may further comprise the step of inserting the conductive exfoliated nano-material into a matrix to form a composite. Suitably, the matrix is a polymer or copolymer selected from the group comprising a thermoplastic, an elastomer or a biopolymer. Preferably, the polymer is an elastomer.

The term "polymer" in the specification should be understood to mean a large molecule (macromolecule) composed of repeating structural units. These subunits are typically connected by covalent chemical bonds. Although the term "polymer" is sometimes taken to refer to plastics, it actually encompasses a large class comprising both natural and synthetic materials with a wide variety of properties. Such polymers may be thermoplastics, elastomers, or biopolymers.

The term "copolymer" should be understood to mean a polymer derived from two (or more) monomeric species, for example a combination of any two of the below-mentioned polymers. An example of a copolymer, but not limited to such, is PETG (Polyethylene Terephthalate Glycol), which is a PET modified by copolymerization. PETG is a clear amorphous thermoplastic that can be injection moulded or sheet extruded and has superior barrier performance used in the container industry.

In one embodiment of the present invention, the polymer is a thermoplastic which may be selected from the group comprising, but not limited to, acrylonitrile butadiene styrene, polypropylene, polyethylene, polyvinylchloride, polyamide, polyester, acrylic, polyacrylic, polyacrylonitrile, polycarbonate, ethylene-vinyl acetate, ethylene vinyl alcohol, polytetrafluoroethylene, ethylene chlorotrifluoroethylene, ethylene tetrafluoroethylene, liquid crystal polymer, polybutadiene, polychlorotrifluoroehtylene, polystyrene, polyurethane, and polyvinyl acetate.

In one embodiment of the present invention, the polymer is an elastomer which may be selected from, but not limited to, the group comprising Polybutadiene, butadiene and acrylonitrile copolymers (NBR), natural and synthetic rubber, polyesteramide, chloropene rubbers, poly(styrene-b-butadiene) copolymers, polysiloxanes (such as Polydimethylsiloxane (PDMS)), polyisoprene, polyurethane, polychloroprene, chlorinated polyethylene, polyester/ether urethane, polyurethane, poly ethylene propylene, chlorosulphanated polyethylene, polyalkylene oxide and mixtures thereof.

In one embodiment of the present invention, the polymer is a biopolymer which may be selected from, but not limited to, the group comprising Gelatin, Lignin, Cellulose, Polyalkylene esters, Polyvinyl alcohol, Polyamide esters, Polyalkylene esters, Polyanhydrides, polylactide (PLA) and its copolymers and polyhydroxyalkanoate (PHA).

In one embodiment of the present invention, the polymer is a copolymer selected from, but not limited to, the group comprising copolymers of propylene and ethylene, Acetal copolymers (Polyoxymethylenes), Polymethylpentene Copolymer (PMP), Amorphous copolyester (PETG), acrylic and acrylate copolymers, polycarbonate (PC) copolymer, Styrene block copolymers (SBCs) to include Poly(styrene-butadiene-styrene) (SBS), Poly(styrene-isoprene-styrene) (SIS), Poly(styrene-ethylene/butylene-styrene) (SEBS), Ethylene vinyl acetate (EVA) and ethylene vinyl alcohol copolymer (EVOH) amongst others.

In one embodiment, the energy applied is sonication.

In one embodiment, the organic solvent in step (a) is selected from the group comprising toluene, cyclohexene, cycloheptane, ethyl-benzene, benzene, carbon tetrachloride, and other solvents with Hansen Solubility Parameters similar to natural rubber.

In one embodiment, the organic solvent in the organic solvent:water mixture is selected from the group comprising N-methylpyrrolidone (NMP), cyclohexylpyrrolidone, dimethyl formamide, Cyclopentanone (CPO), Cyclohexanone, N-formyl piperidine (NFP), Vinyl pyrrolidone (NVP), 1,3-Dimethyl-2-imidazolidinone (DMEU), Bromobenzene, Benzonitrile, N-methyl-pyrrolidone (NMP), Benzyl Benzoate, N,N'-Dimethylpropylene urea, (DMPU), gamma-Butyrlactone (GBL), Dimethylformamide (DMF), N-ethyl-pyrrolidone (NEP), Dimethylacetamide (DMA), Cyclohexylpyrrolidone (CHP), DMSO, Dibenzyl ether, Chloroform, Isopropylalcohol (IPA), Cholobenzene, 1-Octyl-2-pyrrolidone (N8P), 1-3 dioxolane, Ethyl acetate, Quinoline, Benzaldehyde, Ethanolamine, Diethyl phthalate, N-Dodecyl-2-pyrrolidone (N12P), Pyridine, Dimethyl phthalate, Formamide, Vinyl acetate, Acetone.

In one embodiment, the organic solvent:water mixture is a ratio selected from 50:50, 40:60: 30:70, 20:80, or 10:90 (volume:volume).

In one embodiment, the surfactant in the aqueous surfactant solution is selected from the group comprising sodium cholate, sodium deoxycholate, sodium dodecyl sulphate, lithium dodecyl sulphate, ammonium lauryl sulphate, cetyl trimethylammonium bromide, cetyl trimethylammonium chloride, Polyoxyethylene glycol alkyl ethers, Polyoxyethylene glycol octylphenol ethers etc.

In one embodiment, in step (b) of the process described above, the polymer is soaked for about 1 hour to about 48 hours.

In one embodiment, in step (c) of the process described above, the nano-material-incorporated polymer is washed for about 1 minute to about 60 minutes.

In one embodiment, in step (d) of the process described above, the nano-material-incorporated polymer is dried in a vacuum over for about 1 hour to about 24 hours to produce the conductive composite.

In one embodiment, the nano-material is graphene.

In a further embodiment of the present invention, there is provided a device comprising the composite produced by the process described above.

In one embodiment, the device may be selected from, but not limited to, the group comprising electrodes, electrodes, capacitors, transistors, solar cells, dye sensitised solar cells, light emitting diodes, thermoelectric devices, dielectrics, batteries, battery electrodes, capacitor, super capacitors, sensors, strain/motion sensors, nano-transistors, nano-capacitors, nano-light emitting diodes, and nano-solar cells.

In one embodiment, the device is a sensor.

In one embodiment, there is provided a motion or a strain sensor comprising the conductive composite produced by the process described above.

In a further embodiment of the invention, there is provided a method of monitoring or measuring a pulse in a subject, the method comprising the steps of:
  a) attaching a motion or strain sensor as described above to any one of a radial, ulnar, apical, temporal, carotid, brachial, femoral, popliteal or pedal pulse point of the subject; and
  b) monitoring the resistance produced in the sensor over time to monitor or measure the pulse in the subject.

In a further embodiment of the present invention, there is provided a method of monitoring breathing in a subject, the method comprising the steps of:
  (a) attaching a motion or strain sensor as described above to the rib cage of the subject; and
  (b) monitoring the resistance produced in the sensor over time to monitor the breathing in a subject.

BRIEF DESCRIPTION OF THE DRAWINGS

The invention will be more clearly understood from the following description of an embodiment thereof, given by way of example only, with reference to the accompanying drawings, in which:

FIG. 1 illustrates the preparation of graphene infused elastic bands (G-bands). A) As-bought elastic bands. B) Elastic band soaking in toluene. C) A section of an untreated rubber band. D) a band section after soaking in toluene for 3.5 hrs. E) A section of a graphene infused band after soaking in 20% NMP/water mixture for 4 hrs. F-I) Optical micrographs of the surface of an elastic band F) before treatment, G) after soaking in toluene, H) after transfer to NMP and I) after transfer to 20% NMP/water/graphene dispersion. J) Collage of micrographs showing graphene transferred from a treated elastic band fracture surface to a $Si/SiO_2$ wafer. The position of the edge of the fracture surface is marked by the dashed line. The dark dots are graphene as confirmed by the Raman spectrum in K). L) Helium ion micrograph showing rubber-coated graphene flakes protruding from a band fracture surface. M) Measured graphene content (vol %) (after washing) as a function of soak time, $t_s$.

FIG. 2 illustrates the electrical properties of G-bands. A) Measured resistance at zero strain, $R_0$, plotted versus graphene volume fraction. B) Conductivity and Young's modulus (inset) of bands plotted as a function of graphene volume fraction. The lines are fits to the percolation theory. The upper region (solid line) was consistent with a percolation threshold. $\phi_c=0.17\%$ while the lower region (dashed line) was consistent with $\phi_c=0.0\%$, within error. In both cases, the percolation exponent was very close to 2.0. C) Measured resistance as a function of applied strain for bands for two different soak times. The dashed lines represent exponential behaviour. D) Plots of $\Delta R/R_0$ versus strain (log-log scale). The dashed lines show the linear region as defined by $\Delta R/R_0=G\varepsilon$. E) Transverse strain (ie in thickness direction) measured as a function of applied strain (in longitudinal direction). The line is a fit to equation $\varepsilon_t=(\varepsilon+1)^{-\nu}-1$ and is consistent with $\nu=0.5$. F) Estimated resistivity as a function of strain. The dashed lines represents $\rho=\rho_0 e^{g\varepsilon}$.

FIG. 3 illustrates the characteristics of G-band strain sensors. A) Low strain, linear gauge factor, G, plotted versus graphene volume fraction. B) Exponential gauge factor, g, (defined in low strain region by $\rho=\rho_0 e^{g\varepsilon}$) plotted versus graphene volume fraction. C) Linear gauge factor (G) plotted as a function of exponential gauge factor (g). The dashed line is a plot of eq 4 with $\nu=0.5$. The data in A-C) is separated into those mass fractions above (solid symbols)

and below (open symbols) the percolation threshold ($\phi_c$=0.17 vol %). D) Summary of results reported in the literature (see table S1). The maximum reported value of G plotted versus the maximum reported strain. For comparison, the data reported is also plotted as well as data from batches of G-bands not included in FIGS. 2 and 3.

FIG. 4 illustrates the dynamic motion sensing using G-bands. A-B) Resistance change as a response to cyclic strain for the $t_s$=48 hours sample using different strain-time profiles. These can be described by the frequency and the maximum strain rate respectively: A) 0.01 Hz and 1.47%/s, B) 0.33 Hz and 142%/s. C) Resistance data plotted versus cycle number for a triangular strain profile (0.08 Hz and 14.0%/s). D) Photograph of a G-band driven to oscillate perpendicular to its length by a vertically vibrating piston. E) Frequency dependence of the peak to peak resistance change, $\Delta R_{Amp}$. The line represents the behaviour expected for a damped driven piston with the resistance amplitude proportional to the square of the piston amplitude: $\Delta R_{Amp} = \Delta R_{max}(\gamma\nu)^2[(\nu^2-\nu_0^2)^2+(\gamma\nu)^2]^{-1}$ where $\Delta R_{Max}$ is the resistance change on resonance. F) Peak to peak resistance change plotted versus square of piston displacement amplitude. The line is a fit to $\Delta R_{Amp} \propto y_{Amp}^2$. G) Photograph of a twisted band during a torsion experiment. H) Resistance versus twist angle for three different twist rates.

DETAILED DESCRIPTION OF THE DRAWINGS

Materials and Methods

Example 1

A County Stationary No. 32 rubber band was placed in a beaker of toluene in a low power sonic bath (Branson 1510 model 42 kHz) for 3.5 hours. Under these circumstances, the band swells to approximately four times its initial volume. A dispersion of graphene in N-methyl-2-pyrrolidone (NMP) was prepared by ultrasonic tip-sonication (Sonics Vibra Cell model VCX [750 W, 42 kHz]) for 72 Hours at 40% amplitude. This was then vacuum filtered to form a film which was redispersed at high concentration (5 mg/ml) by ultrasonic tip-sonication for 10 minutes followed by bath-sonication for 2.5 hours. To this was added water to give a composition of NMP:water=20:80 by volume (see SI for optimisation of NMP:water ratio). The toluene-treated rubber bands were then directly placed into this dispersion and sonicated in a sonic bath for 4 hours. The treated bands were washed by bath sonication in deionised water for 25 minutes (see SI for optimisation of washing time). After this treatment the rubber band was left to dry in a vacuum oven over-night.

The toluene-swelled bands were soaked in NMP/water for various times from 1-48 hrs and washed in water. Optical micrographs were collected on a Leica microscope using white light illumination and 20× and 50× objectives. Images were recorded with a camera. The Raman measurements were performed using a WITEC alpha300 R Confocal Raman system in air under ambient conditions with the excitation laser line 532 nm. The power of the excitation laser is kept well below 1 mW to avoid heating effect. The Raman emission was collected by an Olympus 100× objective (N.A.=0.8) and dispersed by 600 lines mm-1 gratings. The mass uptake of graphene was found using an accurate balance to measure the mass of the bands before and after treatment with graphene with respect to as mass lost due to the solvent treatment and cleaning.

Figure 5:
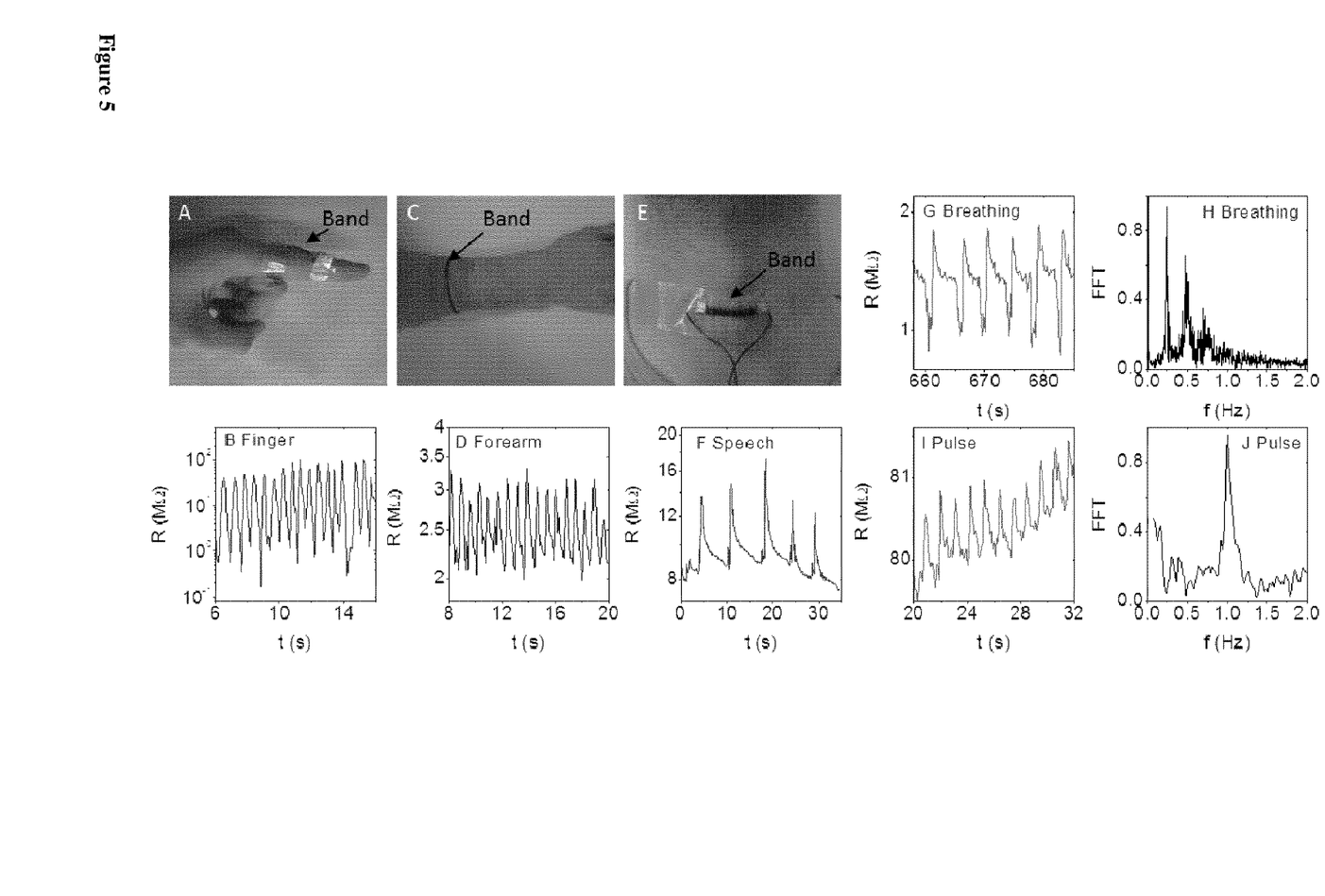
FIG. 5 illustrates applications of G-bands as body monitors. A) Photo of a G-band connected across a knuckle and B) resistance trace as the finger is repeatedly bent. C) Photo of a G-band wrapped around a forearm and D) resistance trace as the hand is repeatedly opened and closed. E) Photo of a G-band attached to a throat and F) resistance trace as the word "graphene" is repeatedly spoken. G) Resistance traces showing slow breathing. H) Fast Fourier transform showing Fourier components of the breathing waveform. I) Resistance traces showing pulse. J) Fast Fourier transform showing Fourier components of the pulse waveform.

Electrical measurements were performed. Samples for electromechanical testing were prepared by cutting the bands into 4 cm segments. Silver paint was applied to the ends of the band to allow for better contact with the conductive clamps holding the band in place. A Zwick Z0.5 ProLine Tensile Tester (100 N Load Cell) was used to apply dynamic strain to the band whilst a Keithley KE2601 source meter, controlled by LabView software, was used to measure the electrical resistance of the band as a function of both strain and time. The bands were first strained very slowly (10 mm/min) until mechanical failure with stress, strain and electrical resistance monitored continuously. This was performed for bands which had been soaked for 1, 4, 8, 16, 21, 24 and 48 hours. In all cases, the washing time was 25 minutes. Following this, dynamic electromechanical testing was performed on bands soaked for 48 hrs (washing time 25 minutes). Saw tooth strain-time profiles were applied as shown in FIG. 5 with resistance and strain monitored as a function of time over 300 cycles. Forearm, hand/finger motion, speech, breathing and pulse was monitored in a similar fashion. The forearm band was directly connected to the source meter via crocodile clip leads attached to the band surface. In the other cases, the leads were attached to adhesive copper tape holding the band in place. For breathing and pulse, the bands were mounted on the chest and the finger tip respectively.

Example 2

A County Stationary No. 32 rubber band was placed in a beaker of toluene in a low power sonic bath (Branson 1510 model 42 kHz) for 3.5 hours. Under these circumstances, the band swells to approximately four times its initial volume. A dispersion of VS2, NbSe2 or TaS2 in N-methyl-2-pyrrolidone (NMP) was prepared by ultrasonic tip-sonication (Sonics Vibra Cell model VCX [750 W, 42 kHz]) for 72 Hours at 40% amplitude. This was then vacuum filtered to form a film which was redispersed at high concentration (5 mg/ml) by ultrasonic tip-sonication for 10 minutes followed by bath-sonication for 2.5 hours. To this was added water to give a composition of NMP:water=20:80 by volume (see SI for optimisation of NMP:water ratio). The toluene-treated rubber bands were then directly placed into this dispersion and sonicated in a sonic bath for 4 hours. The treated bands were washed by bath sonication in deionised water for 25 minutes (see SI for optimisation of washing time). After this treatment the rubber band was left to dry in a vacuum oven over-night.

The toluene-swelled bands were soaked in NMP/water for various times from 1-48 hrs and washed in water. Optical micrographs were collected on a Leica microscope using white light illumination and 20× and 50× objectives. Images were recorded with a camera. The Raman measurements were performed using a WITEC alpha300 R Confocal Raman system in air under ambient conditions with the excitation laser line 532 nm. The power of the excitation laser is kept well below 1 mW to avoid heating effect. The Raman emission was collected by an Olympus 100× objective (N.A.=0.8) and dispersed by 600 lines mm-1 gratings. The mass uptake of VS2, NbSe2 or TaS2 was found using an accurate balance to measure the mass of the bands before and after treatment with VS2, NbSe2 or TaS2 with respect to mass lost due to the solvent treatment and cleaning.

Electrical measurements were performed. Samples for electromechanical testing were prepared by cutting the bands into 4 cm segments. Silver paint was applied to the ends of the band to allow for better contact with the conductive clamps holding the band in place. A Zwick Z0.5 ProLine Tensile Tester (100 N Load Cell) was used to apply dynamic strain to the band whilst a Keithley KE2601 source meter, controlled by LabView software, was used to measure the electrical resistance of the band as a function of both strain and time. The bands were first strained very slowly (10 mm/min) until mechanical failure with stress, strain and electrical resistance monitored continuously. This was performed for bands which had been soaked for 1, 4, 8, 16, 21, 24 and 48 hours. In all cases, the washing time was 25 minutes. Following this, dynamic electromechanical testing was performed on bands soaked for 48 hrs (washing time 25 minutes). Saw tooth strain-time profiles were applied with resistance and strain monitored as a function of time over 300 cycles. Forearm, hand/finger motion, speech, breathing and pulse was monitored in a similar fashion. The forearm band was directly connected to the source meter via crocodile clip leads attached to the band surface. In the other cases, the leads were attached to adhesive copper tape holding the band in place. For breathing and pulse, the bands were mounted on the chest and the fingertip respectively.

Example 3

A County Stationary No. 32 rubber band was placed in a beaker of toluene in a low power sonic bath (Branson 1510 model 42 kHz) for 3.5 hours. Under these circumstances, the band swells to approximately four times its initial volume. A dispersion of carbon nanotubes or silver nanowires in N-methyl-2-pyrrolidone (NMP) was prepared by ultrasonic tip-sonication (Sonics Vibra Cell model VCX [750 W, 42 kHz]) for 72 Hours at 40% amplitude. This was then vacuum filtered to form a film which was redispersed at high concentration (5 mg/ml) by ultrasonic tip-sonication for 10 minutes followed by bath-sonication for 2.5 hours. To this was added water to give a composition of NMP:water=20:80 by volume (see SI for optimisation of NMP:water ratio). The toluene-treated rubber bands were then directly placed into this dispersion and sonicated in a sonic bath for 4 hours. The treated bands were washed by bath sonication in deionised water for 25 minutes (see SI for optimisation of washing time). After this treatment the rubber band was left to dry in a vacuum oven over-night.

The toluene-swelled bands were soaked in NMP/water for various times from 1-48 hrs and washed in water. Optical micrographs were collected on a Leica microscope using white light illumination and 20× and 50× objectives. Images were recorded with a camera. The Raman measurements were performed using a WITEC alpha300 R Confocal Raman system in air under ambient conditions with the excitation laser line 532 nm. The power of the excitation laser is kept well below 1 mW to avoid heating effect. The Raman emission was collected by an Olympus 100× objective (N.A.=0.8) and dispersed by 600 lines mm-1 gratings. The mass uptake of carbon nanotubes or silver nanowires was found using an accurate balance to measure the mass of the bands before and after treatment with carbon nanotubes or silver nanowires with respect to mass lost due to the solvent treatment and cleaning.

Electrical measurements were performed. Samples for electromechanical testing were prepared by cutting the bands into 4 cm segments. Silver paint was applied to the ends of the band to allow for better contact with the conductive clamps holding the band in place. A Zwick Z0.5 ProLine Tensile Tester (100 N Load Cell) was used to apply dynamic strain to the band whilst a Keithley KE2601 source meter, controlled by LabView software, was used to measure the electrical resistance of the band as a function of both strain and time. The bands were first strained very slowly (10 mm/min) until mechanical failure with stress, strain and electrical resistance monitored continuously. This was performed for bands which had been soaked for 1, 4, 8, 16, 21, 24 and 48 hours. In all cases, the washing time was 25 minutes. Following this, dynamic electromechanical testing was performed on bands soaked for 48 hrs (washing time 25 minutes). Saw tooth strain-time profiles were applied with resistance and strain monitored as a function of time over 300 cycles. Forearm, hand/finger motion, speech, breathing and pulse was monitored in a similar fashion. The forearm band was directly connected to the source meter via crocodile clip leads attached to the band surface. In the other cases, the leads were attached to adhesive copper tape holding the band in place. For breathing and pulse, the bands were mounted on the chest and the fingertip respectively.

Results

Figure 1:
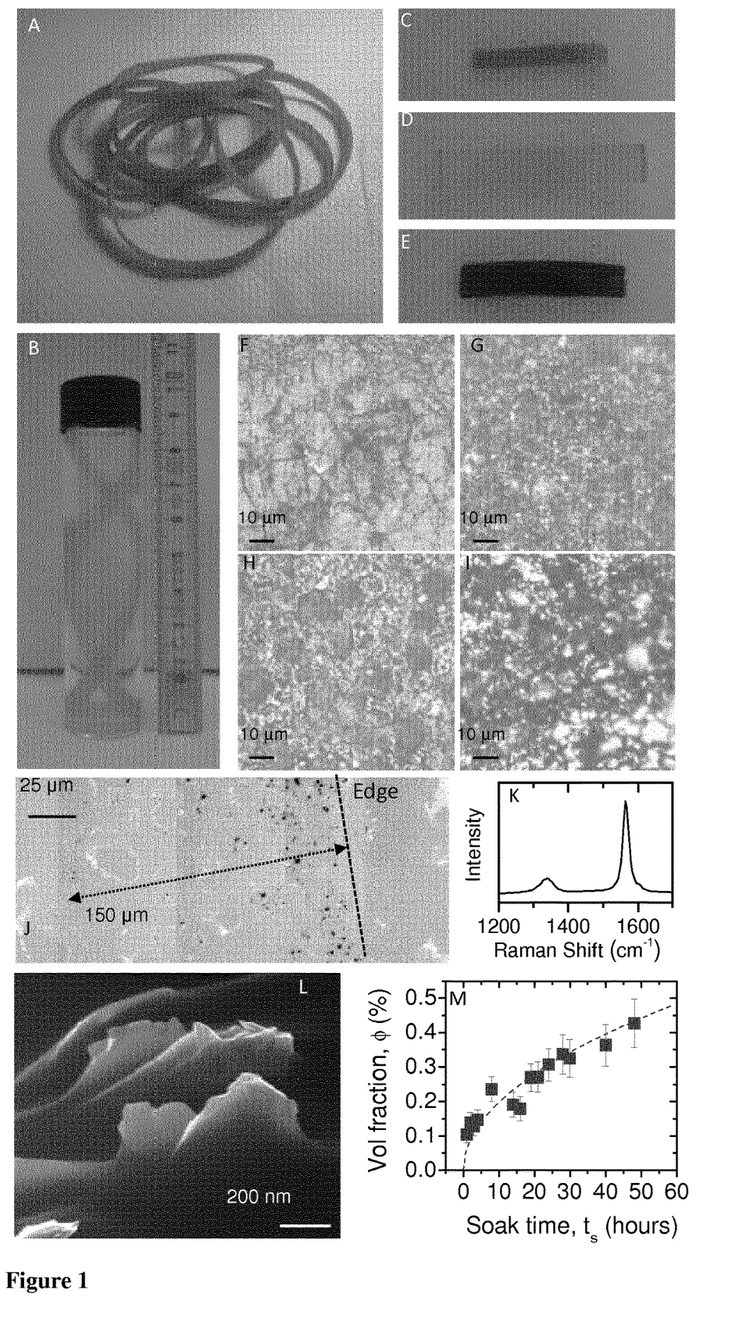

Graphene-elastomer composites with strain sensitive resistance were produced by infusing graphene into elastic bands by soaking in high-concentration graphene-solvent dispersions. The elastic bands (FIG. 1A) were sourced from County Stationary (No. 32, 1.45×2.75×76 mm-thickness×width×circumference) and consisted primarily of natural rubber. To achieve infusion, the bands must first be treated to open pores to allow entry of the graphene platelets. This was achieved by soaking the bands in toluene (FIG. 1B) for 3.5 hours in a sonic bath (Branson 1510). Toluene was chosen because its Hansen solubility parameters ($\delta_D=18$ MPa$^{1/2}$, $\delta_P=1.4$ MPa$^{1/2}$, $\delta_H=2$ MPa$^{1/2}$) are relatively close to those of natural rubber ($\delta_D=17.4$ MPa$^{1/2}$, $\delta_P=3.1$ MPa$^{1/2}$, $\delta_H=4.1$ MPa$^{1/2}$). These parameters are related to the dispersive ($\delta_D$), polar ($\delta_P$) and H-bonding ($\delta_H$) components of a materials cohesive energy density and are a measure of intermolecular binding strength. For two systems to mix/interact effectively on the molecular scale, all three Hansen parameter must be close, usually within a few MPa$^{1/2}$. This is clearly the case for toluene and natural rubber and it is well-known that toluene readily diffuses into the interior of natural rubber. This results in considerable swelling of the band (FIG. 1C-D) with all dimensions increasing by factors of ×1.5-1.6 after 3.5 hours soaking. This is consistent with a decrease in density from 930 kg/m$^3$ for natural rubber to ~250 kg/m$^3$ after 3.5 hrs soaking resulting in the introduction of ~73% porosity (FIG. 1 A-B). Other solvents with Hansen parameters similar to natural rubber can also be used. Examples include cyclohexene, cycloheptane, ethylbenzene, benzene, carbon tetrachloride etc.

Graphene can be infused into the open pores simply by soaking in high concentration graphene dispersions (see Materials and Methods). It is well known that graphite can be exfoliated under sonication to give dispersions of graphene nanosheets in solvents such as N-methyl-pyrrolidone (NMP). However, it was found that soaking of elastic bands in NMP-graphene dispersions did not result in significant uptake of graphene by the bands. This is probably because it is more energetically favourable for the graphene to remain in the NMP than diffuse into the porous interior of the band. This can be understood by considering the Hansen parameters of graphene ($\delta_D$=18 MPa$^{1/2}$, $\delta_P$=9.3 MPa$^{1/2}$, $\delta_H$=7.7 MPa$^{1/2}$) and NMP ($\delta_D$=18 MPa$^{1/2}$, $\delta_P$=12.3 MPa$^{1/2}$, $\delta_H$=7.2 MPa$^{1/2}$). The Hansen parameters of graphene (particularly $\delta_P$ and $\delta_H$) are much closer to those of NMP than to natural rubber. This means it is more energetically favourable for the graphene to be surrounded with NMP than natural rubber and so it is unlikely that the graphene will diffuse into the pores in the rubber. To address this problem, it was made less energetically favourable for the graphene to remain dispersed in NMP by adding water to the graphene-NMP dispersion. The Hansen parameters of water ($\delta_D$=15.5 MPa$^{1/2}$, $\delta_P$=16 MPa$^{1/2}$, $\delta_H$=42 MPa$^{1/2}$) are very different from those of NMP. On adding water to NMP, the solvent mixture is described by solubility parameters which are approximately the weighted mean of those of the components. For example a 20:80 NMP:water mixture will have the following Hansen parameters ($6_D$=16 MPa$^{1/2}$, $\delta_P$=15.3 MPa$^{1/2}$, $\delta_H$=35 MPa$^{1/2}$). These are significantly different to those of graphene, making it more favourable for the graphene to diffuse into the rubber. After soaking in an NMP:water mixture for a pre-determined soak time (typically 1-48 hrs), the bands were removed and washed by briefly sonicating in water. On drying it was found that the band had shrunk relative to its swollen state but typically did not return to its original size (FIG. 1E). In addition, the bands had changed colour, taking on a much darker hue typical of polymer-graphene composites.

The effect of soaking was investigated by performing optical microscopy on the surface of the bands. Shown in FIG. 1F is an optical image of an untreated band. The rubber appears to display structure on length scales of a few microns to tens of microns. It is suggested that this reflects the fact that natural rubber consists of latex particles with a range of diameters up to a few microns. After soaking in toluene, followed by drying in a vacuum oven for 12 hours, (FIG. 1G) this structure is less visible perhaps suggesting some coalescence of the latex particles. However, after soaking in toluene followed by soaking in NMP:water (20:80) (FIG. 1H) circular pits, typically a few microns in diameter can clearly be seen. This suggests that these represent latex particles or particles clusters which have been removed from the surface under sonication in the NMP:water mixture. This is plausible as the latex particles comprising natural rubber tend to be coated by a mixture of proteins which can interact strongly with water. FIG. 1I shows these pits to also be present after soaking in NMP:water/graphene dispersion. This suggests that the water plays a dual role. In addition to driving the graphene out of dispersion, it may act to weaken the bonds between latex particles. This could introduce gaps between particles. Eventually, these gaps might coalesce into an inter-connected porous network with pore size large enough for graphene to diffuse into.

This hypothesis was tested by investigating whether graphene actually reaches the interior of the network rather than remaining solely on the surface. This was more challenging than expected. Initial attempts to image fracture surfaces of bands broken after dipping in liquid $N_2$ showed nothing. Attempts to map the fracture surface with Raman spectroscopy failed due to severe heating of the rubber under the beam. To avoid such heating effects, the freeze-fractured surfaces were stamped onto scotch tape and transferred the material adhered from the scotch tape to Si/SiO$_2$ wafers (200 nm oxide) in a manner similar to micromechanical cleavage of graphite.

The material which has been transferred into the wafer can easily be imaged optically and characterised with Raman spectroscopy. As shown in FIG. 1J a number of blue-green spots can be seen close to the position of the wafer associated with the edge of the band (dashed line). Raman spectroscopy (FIG. 1K) shows these spots to be a few layers of graphene. In all cases, such graphene flakes were found within ~0.3 mm from the edge of the rubber band. This penetration depth is most likely an underestimation, due to the difficulties in transferring the embedded material. Also observed were very faint vibrational modes attributed to natural rubber (1260, 1442, 2848, 2882 cm$^{-1}$) in some areas of the wafer, suggesting that both graphene and rubber were transferred in the stamping process. This would be expected if graphene flakes which were embedded in the rubber were transferred rather than just graphene which had become adhered during fracture or handling.

It can be confirmed that graphene is embedded in the rubber by investigating the fracture surface using Helium ion microscopy. This technique resembles SEM but is much more effective for imaging low conductivity surfaces. Shown in FIG. 1I is a Helium ion micrograph of a graphene flake protruding from a band fracture surface. This flake was observed approximately 200 μm from the band edge and is clearly embedded in the rubber. This confirms that graphene can enter the interior of the band under the conditions described above.

By carefully weighing the bands after soaking, washing and drying, graphene uptake as a function of soak time was measured. This data is shown in FIG. 1M and confirms that the graphene mass fraction increases steadily with soak time, reaching 0.63 wt % after 48 hrs. Empirically, the mass fraction increases as $t_s^{1/2}$. This behaviour has been observed previously for carbon nanotube buckypaper soaked in polymer solutions.

Figure 2:
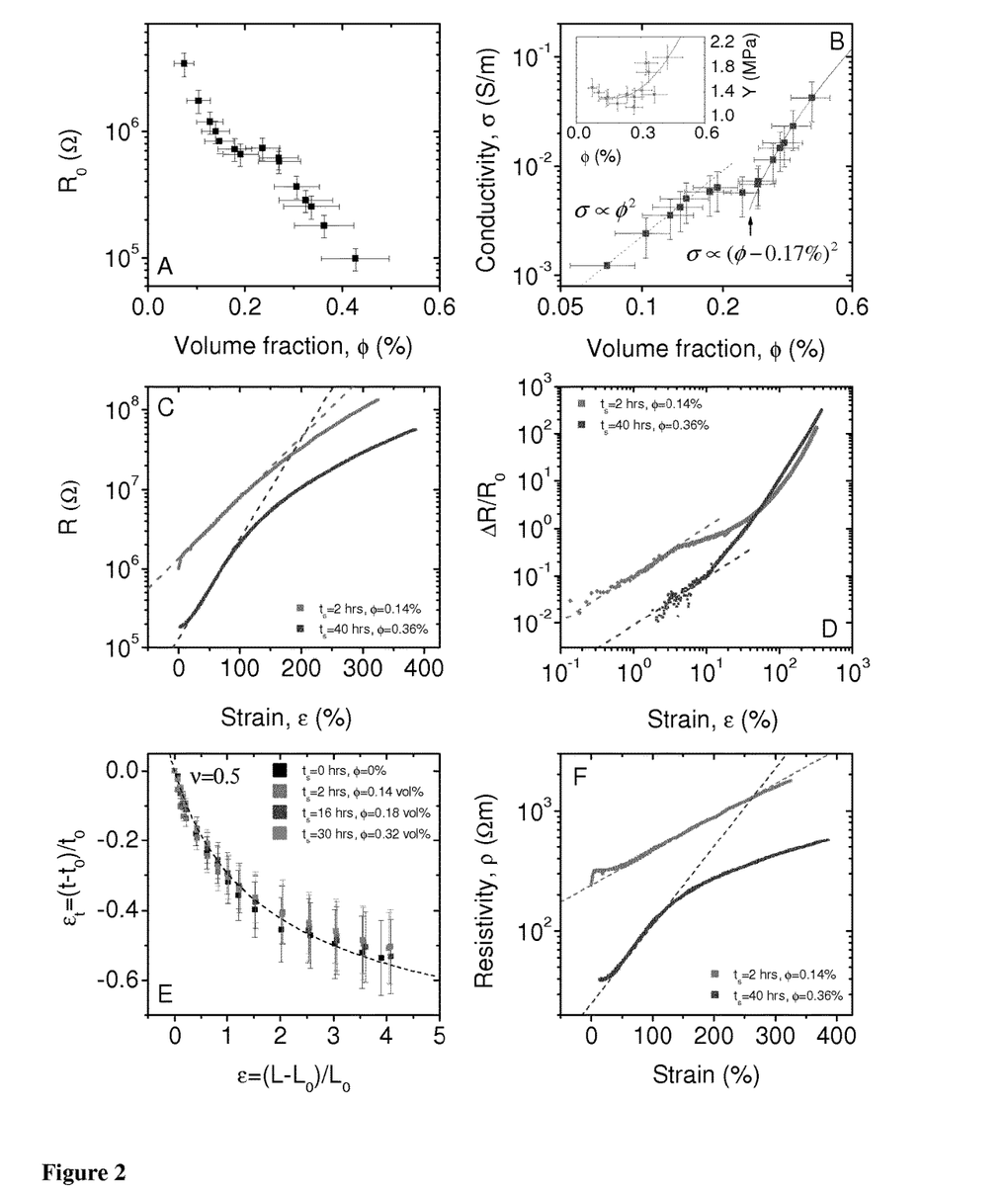

For each of the soak times, the (unstrained) electrical resistance, $R_0$, was measured which is plotted as a function of graphene volume fraction in FIG. 2A. The resistance varies from 3.5 MΩ at very low volume fraction ($t_s$=30 min) to 98 kΩ at $\phi$=0.43% ($t_s$=48 hrs). To better understand this, the conductivity, σ, was plotted as a function of volume fraction in FIG. 2B. This data clearly shows two regimes, one on either side of $\phi \approx 0.2\%$. The upper range ($\phi$>0.2%) is consistent with percolation theory and is described by the percolation scaling law: $\sigma = \sigma_0(\phi-\phi_c)^t$ where $\phi_c$ is the percolation threshold and t is the percolation exponent. Fitting gives $\phi_c$=0.17, close to values previously reported for solution cast polymer-graphene composites and consistent with the value of $\phi_c$~0.1% expected theoretically for isotropic distributions of nanosheets with aspect ratio ~1000. In addition, t=2.0, identical to the universal 3-dimensional percolation exponent.

However, the lower range ($\phi$<0.2%) shows higher conductivity than would be expected given the measured percolation threshold quoted above. Interestingly, this data fits well to a second percolation scaling law, again with t=2.0 but with percolation threshold indistinguishable from zero. The presence of a second percolation threshold is rather unusual but has been observed in systems where current can flow for $\phi<\phi_c$, due to tunnelling between physically disconnected particles. This implies that a physically connected network of nanosheets only forms at $\phi_c$=0.17. This is supported by data which shows the modulus, Y, of the G-bands to remain roughly constant before increasing for values of $\phi$>0.2% (FIG. 2B inset). This is consistent with mechanical percolation where stiffening only occurs when a connected network forms. Indeed, it was found that the modulus data is well fit by the mechanical percolation equation $(Y-Y_{matrix} \propto (\phi-\phi_c)^t$ with $Y_{matrix}=1.3$ MPa, $\phi_c=0.17\%$ and $t=2.0$ (solid red line).

Whether the graphene nanosheets are physically touching to form a continuous network or not, it is expected that the electrical resistance to increase on the application of strain due to the divergence of adjacent nanosheets. Strain was applied slowly (10 mm/min) to G-bands with a range of volume fractions. In all cases the resistance increased exponentially at low to intermediate strains as described empirically by $R=R_0e^{\gamma\varepsilon}$, where $\gamma$ varied from 1-2 at low $\phi$ to 3-4 at higher $\phi$. Although the resistance increased more slowly at strains above ~100-200% (FIG. 2C), in some cases the total resistance increase was almost three orders of magnitude for strains of $\varepsilon>500\%$. In addition, $\Delta R/R_0$ was found to scale linearly with E at low strain for all samples (FIG. 2D), giving values of up to G=16 in the main batch used in the experiments described herein. However, some batches of G-bands displayed values of G as high as 30.

In order to understand the strain-induced resistance changes, it is necessary to differentiate strain-induced dimensional changes from flake separation effects. For strain sensitive materials in general, one can relate the fractional resistance change to the strain by:

$$\frac{\Delta R}{R_0} = (1+2v)\varepsilon + \frac{\Delta\rho(\varepsilon)}{\rho_0} \quad (1)$$

where the first term describes the effects of dimensional changes while the second term describes the effects of any strain dependence of the resistivity. Thus it is important to understand the effect of strain on the intrinsic material resistivity. For nano-composites, the resistivity will increase with strain as the nano-conductors are pulled apart. Specifically, the inter-nanosheet charge transport will be by tunnelling, allowing one to write as effective inter-nanosheet resistance as $R_J \propto e^{\beta d}$ where d is the inter-nanosheet distance and $\beta$ is a constant which depends on the details of the inter-nanosheet potential barrier. In nano-structured systems, such junction resistances tend to control the electrical properties such that $\rho \propto R_J$. It is assumed that the inter-nanosheet separation scales with sample length on stretching which implies that $\varepsilon=(d-d_0)/d_0$, where $d_0$ is the unstrained inter-nanosheet separation. Combining these equations to eliminate $R_J$ and d gives:

$$\rho = \rho_0 e^{g\varepsilon} \quad (2)$$

where g is denoted as the exponential gauge factor as defined by $g=\beta d_0$.

To test this prediction, the strain dependent resistivity must be obtained. This requires knowledge of Poisson's ratio, which is obtained be measuring changes in G-band thickness, t, as a function of band length, L, for four volume fractions, as shown in FIG. 2E. As expected, the transverse strain, $\varepsilon_t=(t-t_0)/t_0$, scaled with longitudinal strain, $\varepsilon=(L-L_0)/L_0$, as $\varepsilon_t=(\varepsilon+1)^{-v}-1$, with fitting giving v=0.5 for all bands. This is consistent with the strained G-band thickness, t, width, w and length, L, being interrelated by $t/t_0=w/w_0=(L/L_0)^{-v}$ where $t_0$, $w_0$ and $L_0$ are the unstrained dimensions. This allows the intrinsic resistivity to be estimated as a function of strain using $$\rho(\varepsilon) = R(\varepsilon)\frac{tw}{L} = R(\varepsilon)\frac{t_0w_0}{L}(\varepsilon+1)^{-(2v+1)} \quad (3)$$

The strain dependent resistivity, calculated in this way is shown in FIG. 2F for two representative G-bands. For low volume fractions, $\rho$ scales exponentially with $\varepsilon$ over the entire strain range as predicted by equation 2. However, for $\phi \geq \phi_c$ the resistivity increase slows at strains above ~100%, possibly due to jamming or rotational effects. Fitting gave values of g from 0-1 at low $\phi$ to 2-3 at higher $\phi$.

In the low-strain region, equation 2 can be expanded to give $\Delta\rho/\rho_0=g\varepsilon$. Substituting this into equation 1 gives $$\frac{\Delta R}{R_0} = (1+2v+g)\varepsilon \quad (4)$$

Applying the definition of gauge factor, G, predicts a relationship between linear and exponential gauge factors:

$$G = 1+2v+g \quad (5)$$

Figure 3:
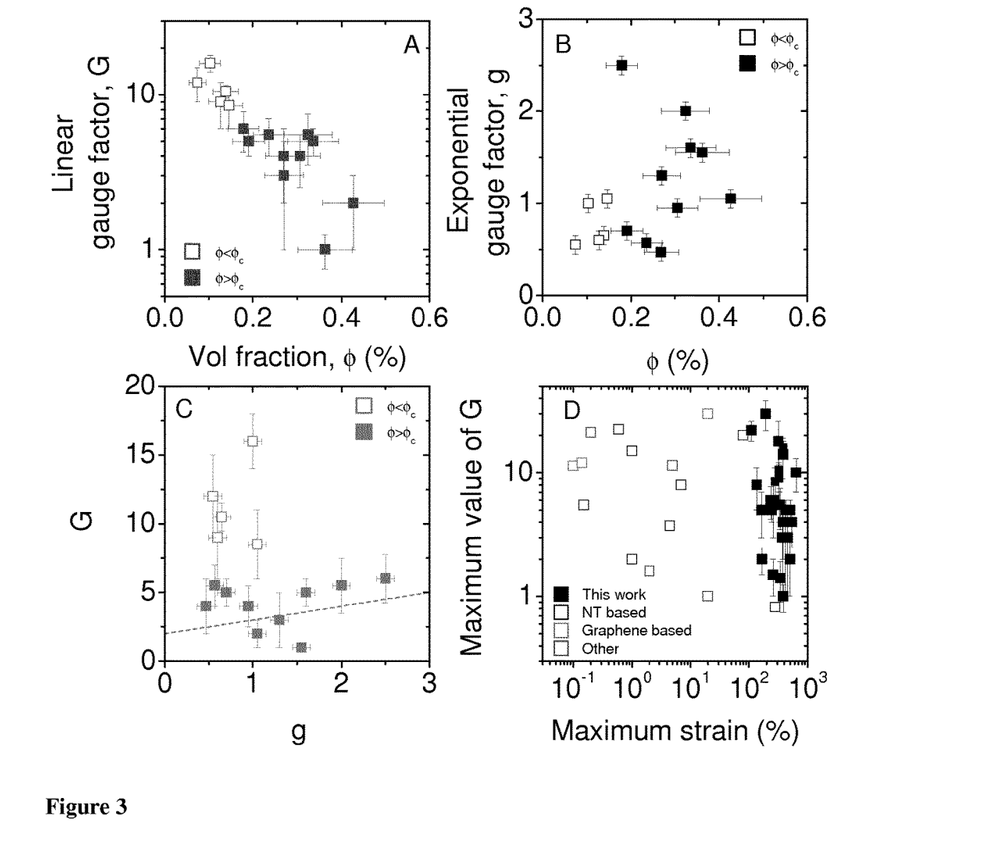

The gauge factor, G, was plotted as a function of graphene volume fraction, $\phi$, in FIG. 3A. As has been observed for previous nano-composite strain gauges, G increases sharply as the volume fraction is reduced with values as high as G=16 observed for samples with $\phi<\phi_c$. A plot of g versus $\phi$, as shown in FIG. 3B, shows it to increase with volume fraction. As described above, it was expected that $g=\beta d_0$. For $\phi \geq \phi_c$ the nanosheets form a connected network, meaning do should be constant. Thus, increases in g with $\phi$ imply $\beta$ and so the potential barrier to vary with $\phi$. In addition, it was found that the exponential factor, $\gamma$, which controls the strain dependence of resistance, to scale empirically with g as: $\gamma \approx g+1$.

Taking v=0.5, the prediction of equation 5 was tested in FIG. 3C, finding good agreement for composites above the percolation threshold. Below the percolation threshold, anomalously high values of G are found for reasons which are not understood. However, this data has clear implications: if high strain sensitivity (i.e. high $\Delta R/R_0$) is required at low strain, then composites with $\phi<\phi_c$ are required while if high sensitivity at high strain is required (i.e. high g) larger values of $\phi$ are needed.

Because of the relationship between G and g, G as a figure of merit can be used for the sensitivity of strain sensors in both the high and low strain regimes. However, the vast majority of strain-sensing materials are relatively brittle and so unsuited to high-strain sensing. Thus, a combination of high g and high failure-strain is required for any versatile strain sensing material. In FIG. 3D, a map of the maximum reported values of both G and operating strain were plotted for a range of strain sensors from both the literature and the study described here. It was found that the best G-band strain sensors to have comparable gauge factors to the best high-strain ($\varepsilon>10\%$) sensors. However, the best G-bands described here work at considerably higher stains then even the most ductile strain sensors reported to date (635% versus 280%).

Figure 4:
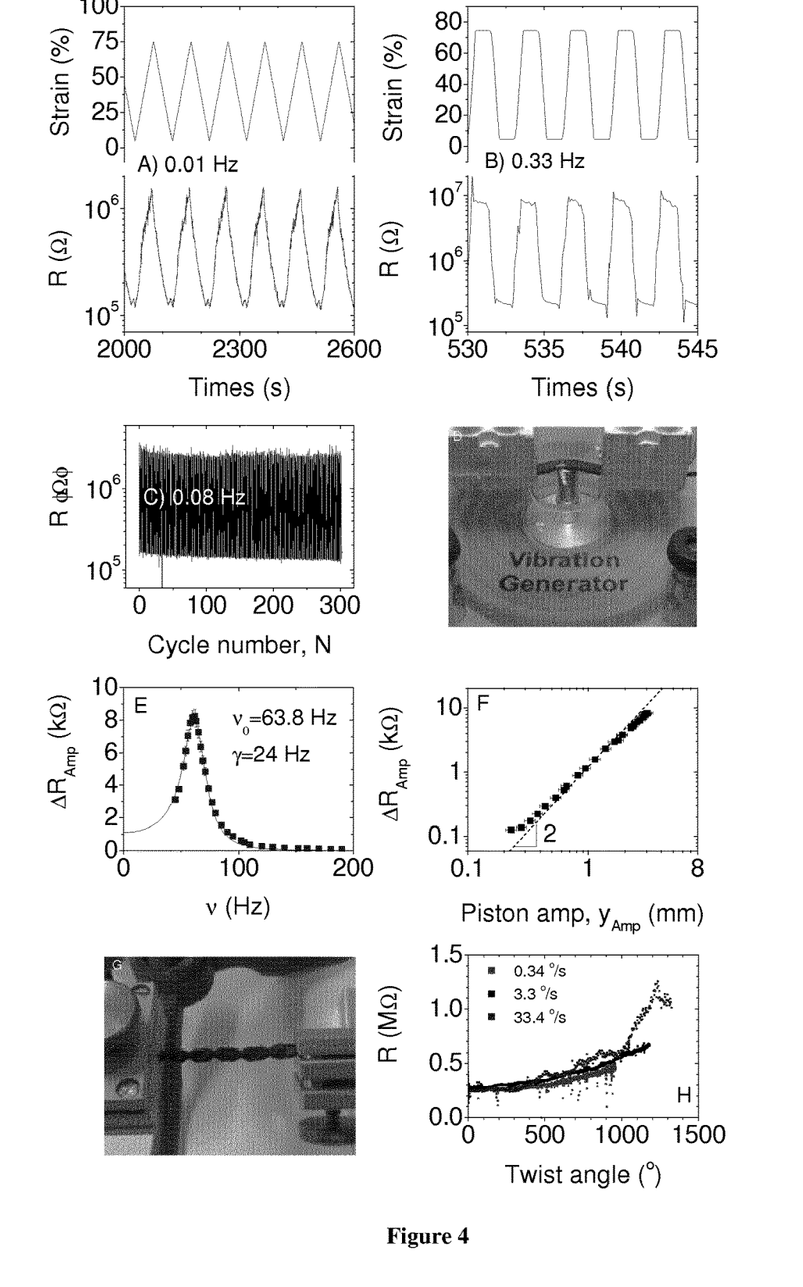

The combination of high sensitivity and ductility suggests G-bands to be ideal for dynamic strain sensing. To test this, a tensile tester was used to subject G-bands to a number of cyclic strain profiles with frequencies and maximum strain rates in the range 0.01-0.33 Hz and 1.47-142%/s respectively. As shown in FIGS. 4A and B, log(R) followed the strain extremely well with little degradation over at least 300 cycles (FIG. 4C). In particular, the sample tested at 0.33 Hz displayed a maximum value of $\Delta R/R_0=40$ at $\varepsilon=75\%$. This behaviour is consistent with g=4-5 and is competitive with the best nano-composite strain sensors which operate at strains above 1%. For comparison, Park et al. (Highly stretchable electric circuits from a composite material of silver nanoparticles and elastomeric fibres. *Nat. Nanotechnol.* 7, 803-809, (2012)) demonstrated silver nano-particle/elastomer composites which operated at 1 Hz displaying maximum values of $\Delta R/R_0=3$ strains up to 16%.

In the experiments described above, the frequency range was limited by the tensile tester used. To explore the sensor response at higher frequencies we used a commercial vibration generator to drive a piston which oscillated the band perpendicular to its length (FIG. 4D). Using a travelling microscope we could show that, with the band in place, the piston oscillated like a damped, driven linear oscillator with amplitude, $y_{Amp}$, which varied with frequency, $\nu$, as $y_{Amp}=y_{Res}\,\gamma\nu/[(\nu^2-\nu_0^2)^2+(\gamma\nu)^2]^{1/2}$ where $y_{Amp}=3.0$ mm was the resonant amplitude, $\gamma=22$ Hz was the damping constant and $\omega_0=63.5$ Hz was the resonant frequency. In this geometry and at low strain, the strain amplitude is given by $\varepsilon_{Amp}\approx 2y_{Amp}^2/L_0^2$. Using an oscilloscope, the amplitude of resistance oscillation, $\Delta R_{Amp}$, as a function of frequency was monitored, as shown in FIG. 4E. Assuming linear behaviour, the resistance amplitude is expected to be given by $$\Delta R_{Amp} \approx 2R_0 G y_{Amp}^2/L_0^2. \quad (6)$$

As such the data was fitted in FIG. 4E to $$\Delta R = \frac{\Delta R_{Res}(\gamma\nu)^2}{[(\nu^2-\nu_0^2)^2+(\gamma\nu)^2]} \quad (7)$$

(i.e. $\propto y_{Amp}^2$) where $\Delta R_{Res}=7.8$ k$\Omega$, is the resistance amplitude on resonance and $\gamma=24$ Hz and $\omega_0=63.8$. It was noted that the fit is very good over all frequencies, even close to resonance where the G-band is subjected to velocities, tensile strains and strain rates of approximately 1.2 m/s, 6% and 7000%/s, respectively. $\Delta R_{Amp}$ versus $\propto y_{Amp}$ was plotted in FIG. 4F, showing good agreement with equation 6 consistent with $G=2.8$, approximately independent of frequency. It is noted that the sensitivity of this G-band remains undiminished at frequencies of up to 200 Hz. This is believed to be the highest frequency nano-composite strain sensor yet demonstrated.

The ability of G-bands to respond to torsion was also tested (FIG. 4G). Measureable changes in resistance were detected giving values of $\Delta R/R_0$ up to 12 for twist angles of up to 1300° at rotation rates of up to at least 33°/s.

The Applicants believe G-bands to be of great interest in a range of applications but in particular as components in medical devices for measuring human (or animal) motion and for monitoring in a range of areas from motion of athletes to rehabilitation to general well-being. To demonstrate the broad dynamic range of the G-bands, the G-bands of the present application were tested as strain sensors in a number of scenarios. By attaching a G-band across the first knuckle of the index finger (FIG. 5A), the relatively high-strain motion ($\varepsilon$-40%) associated with repeated bending of the finger could be monitored (FIG. 5B). Muscular motion associated with clenching and unclenching of the first ($\varepsilon$~4%) was also monitored by wrapping a G-band around the forearm (FIGS. 5C&D). By attaching the G-Band to the throat (FIG. 5E) speech could be detected (FIG. 5F), in this case repeated enunciation of the word "graphene". It was noted that the G-band is so sensitive that care must be taken by the subject to remain still or small neck movements will dominate the response rendering the throat movement associated with speech undetectable.

In order to clearly demonstrate the sensitivity and potential of G-bands as dynamic strain sensors, it was attempted to measure the very subtle motions associated with breathing and pulse. To monitor breathing, a ~3 cm long G-band was attached horizontally across the rib cage on the subjects side. The resistance was monitored over approximately 5 minutes with the subject sitting in a chair. A section of the resistance-time waveform is shown in FIG. 5G. A well-defined, asymmetric, periodic response can clearly be seen. The Fourier transform (FIG. 5H) clearly shows the Fourier components associated with the breathing movement. More challenging was the measurement of pulse. Here a band which displayed particularly low current noise was wrapped around the tip of the subject's finger with a few 10s of percent pre-strain. Under these circumstances, a symmetric, periodic waveform was detected (FIG. 5I) with a frequency of ~1 Hz and a single Fourier component (FIG. 5J) as expected for human pulse.

As demonstrated herein, the technical advantages of the sensors produced by the very simple method of the subject application, which infiltrates commercially available elastic bands with liquid-exfoliated graphene to produce versatile strain sensors, are (i) the observed gauge factors are up to 30, which is much higher than most; (ii) strains can be operated up to 600%, both under quasi-static conditions or at dynamic strain rates of at least 7000%/s, which is much higher than most; and (iii) the sensors can sense fast motion—up to 200 Hz, which is 20-times faster than currently observed sensors of this type. This is also believed to be the highest frequency nano-composite strain sensor yet demonstrated. An impressive performance as kinesthetic motion sensors, detecting motions as subtle as those associated with breathing and pulse, have also been demonstrated.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A process for producing a conductive composite, the process comprising:
   a) soaking an elastomer in an aqueous surfactant solution or an organic solvent, the elastomer selected from the group consisting of polybutadiene, butadiene and acrylonitrile copolymers (NBR), natural and synthetic rubber, polyesteramide, chloroprene rubbers, poly(styrene-b-butadiene) copolymers, polysiloxanes, polyisoprene, polyurethane, polychloroprene, chlorinated polyethylene, polyester/ether urethane, polyethylene propylene, chlorosulphanated polyethylene, polyalkylene oxide, and mixtures thereof;
   b) further soaking the elastomer from step (a) in a solution of conductive nano-material dispersed in an aqueous surfactant solution or an organic solvent:water mixture such that the conductive nano-material is incorporated into the elastomer structure, the conductive nano-material being an exfoliated 2-dimensional material obtained from exfoliating a 3-dimensional layered compound or a 1-dimensional material selected from the group consisting of carbon nanotubes and metallic nanowires, the metallic nanowires including silver nanowires, platinum nanowires, gold nanowires, and palladium nanowires;

c) washing the conductive nano-material-incorporated elastomer in deionized water; and d) drying the washed composite nano-material-incorporated elastomer to produce the conductive composite, wherein the conductive composite incorporates the conductive nano-material throughout the structure of the elastomer without affecting the integrity of the properties of the elastomer; further wherein energy is applied to each of steps (a), (b), and (c).

2. The process according to claim 1, wherein the conductive nano-material is an exfoliated 2-dimensional material obtained from exfoliating a 3-dimensional layered compound and wherein the 3-dimensional layered compound is graphite.

3. The process according to claim 1, wherein the conductive nano-material is an exfoliated 2-dimensional material obtained from exfoliating a 3-dimensional layered compound and wherein the 3-dimensional layered compound is a transition metal dichalcogenide having the formula $MX_n$, a layered material comprising transition metal oxides, boron nitride (BN), $Bi_2Te_3$, $Sb_2Te_3$, $TiNCl$, and $MoO_3$, or an inorganic layered compound, wherein M is selected from the group consisting of Ti, Zr, Hf, V, Nb, Ta, Cr, Mn, Mo, W, Tc, Re, Ni, Pd, Pt, Fe, and Ru; X is selected from the group consisting of O, S, Se, and Te, and $1 \leq n \leq 3$.

4. The process according to claim 1, wherein the conductive nano-material is an exfoliated 2-dimensional material graphene.

5. The process according to claim 1, wherein the conductive nano-material is an exfoliated 2-dimensional material graphene, wherein the exfoliated graphene is used for at least one of mechanical reinforcement of elastomers, reduction in permeability of elastomers, enhancement of electrical conductivity and/or thermal conductivity of elastomers, and production of conductors and electrode materials.

6. The process according to claim 1, wherein the energy applied is sonication.

7. The process according to claim 1, wherein the organic solvent in step (a) is selected form the group consisting of toluene, cyclohexene, cycloheptane, ethyl-benzene, benzene, and carbon tetrachloride.

8. The process according to claim 1, wherein the organic solvent in the organic solvent:water mixture is selected from the group consisting of N-methylpyrrolidone (NMP), cyclohexylpyrrolidone, di-methyl formamide, Cyclopentanone (CPO), Cyclohexanone, N-formyl piperidine (NFP), Vinyl pyrrolidone (NVP), 1,3-Dimethyl-2-imidazolidione (DMEU), Bromobenzene, Benzonitrile, N-methyl-pyrrolidone (NMP), Benzyl Benzoate, N,N'-Dimethylpropylene urea[H] (DMPU), gamma-Butyrlactone (GBL), Dimethylformamide (DMF), N-ethyl-pyrrolidone (NEP), Dimethylacetamide (DMA), Cyclohexylpyrrolidone (CHP), DMSO, Dibenzyl ether, Chloroform, Isopropylalcohol (IPA), Chlorobenzene, 1-Octyl-2-pyrrolidone (N8P), 1-3 dioxolane, Ethyl acetate, Quinoline, Benzaldehyde, Ethanolamine, Diethyl phthalate, N-Dodecyl-2-pyrrolidone (N12P), Pyridine, Dimethyl phthalate, Formamide, Vinyl acetate, and Acetone.

9. The process according to claim 1, wherein the organic solvent:water mixture is a ratio selected from 50:50, 40:60, 30:70, 20:80, or 10:90 (volume:volume).

10. The process according to claim 1, wherein the surfactant in the aqueous surfactant solution of (a) and (b) is selected from the group consisting of sodium cholate, sodium deoxycholate, sodium dodecyl sulphate, lithium dodecyl sulphate, ammonium lauryl sulphate, cetyl trimethylammonium bromide, cetyl trimethylammonium chloride, Polyoxyethylene glycol alkyl ethers, and Polyoxyethylene glycol octylphenol ethers.

11. The process according to claim 1, wherein in step (b), the elastomer is soaked for about 1 hour to about 48 hours; and wherein in step (c), the nano-material-incorporated elastomer is optionally washed for about 1 minute to about 60 minutes; and wherein in step (d), the nano-material-incorporated elastomer is optionally dried in a vacuum over for about 1 hour to about 24 hours to produce the conductive composite.

12. A device comprising:
a conductive composite produced by a process comprising:
a) soaking an elastomer in an aqueous surfactant solution or an organic solvent, the elastomer selected from the group consisting of polybutadiene, butadiene and acrylonitrile copolymers (NBR), natural and synthetic rubber, polyesteramide, chloroprene rubbers, poly(styrene-b-butadiene) copolymers, polysiloxanes, polyisoprene, polyurethane, polychloroprene, chlorinated polyethylene, polyester/ether urethane, polyethylene propylene, chlorosulphanated polyethylene, polyalkylene oxide, and mixtures thereof;
b) further soaking the elastomer from step (a) in a solution of conductive nano-material dispersed in an aqueous surfactant solution or an organic solvent:water mixture such that the conductive nano-material is incorporated into the elastomer structure, the conductive nano-material being an exfoliated 2-dimensional material obtained from exfoliating a 3-dimensional layered compound or a 1-dimensional material selected from the group consisting of carbon nanotubes and metallic nanowires, the metallic nanowires including silver nanowires, platinum nanowires, gold nanowires, and palladium nanowires;
c) washing the conductive nano-material-incorporated elastomer in deionized water; and
d) drying the washed composite nano-material-incorporated elastomer to produce the conductive composite, wherein energy is applied to each of steps (a), (b), and (c) and further wherein the conductive composite incorporates the conductive nano-material throughout the structure of the elastomer without affecting the integrity of the properties of the elastomer.

13. A method of monitoring a pulse or breathing in a subject, the method comprising:
a) attaching a motion or strain sensor to any one of a radial, ulnar, apical, temporal, carotid, brachial, femoral, popliteal, rib cage or pedal pulse points of the subject, wherein the motion or strain sensor comprises a conductive composite produced by a process comprising:
i) soaking an elastomer in an aqueous surfactant solution or an organic solvent, the elastomer selected from the group consisting of polybutadiene, butadiene and acrylonitrile copolymers (NBR), natural and synthetic rubber, polyesteramide, chloroprene rubbers, poly(styrene-b-butadiene) copolymers, polysiloxanes, polyisoprene, polyurethane, polychloroprene, chlorinated polyethylene, polyester/ether urethane, polyethylene propylene, chlorosulphanated polyethylene, polyalkylene oxide, and mixtures thereof;
ii) further soaking the elastomer from step (a) in a solution of conductive nano-material dispersed in an aqueous surfactant solution or an organic solvent:water mixture such that the conductive nano-material is incorporated into the elastomer structure, the conductive nano-material being an exfoliated 2-dimensional material obtained from exfoliating a 3-dimensional layered compound or a 1-dimensional material selected from the group consisting of carbon nanotubes and metallic nanowires, the metallic nanowires including silver nanowires, platinum nanowires, gold nanowires, and palladium nanowires;

iii) washing the conductive nano-material-incorporated elastomer in deionized water; and iv) drying the washed composite nano-material-incorporated elastomer to produce the conductive composite, wherein energy is applied to each of steps (i), (ii), and (iii) and further wherein the conductive composite incorporates the conductive nano-material throughout the structure of the elastomer without affecting the integrity of the properties of the elastomer; and b) monitoring the resistance produced in the sensor over time to monitor or measure (i) the pulse of the subject or (ii) the breathing of the subject.

14. The device of claim 12 wherein the device is at least one of: an electrode, a capacitor, a transistor, a solar cell, a dye sensitized solar cell, a light emitting diode, a thermoelectric device, a dielectric, a battery, a battery electrode, a capacitor, a super capacitor, a sensor, a strain sensor, a motion sensor, a nano-transistor, a nano-capacitor, a nano-light emitting diode, and a nano-solar cell.

* * * * *

UNITED STATES PATENT AND TRADEMARK OFFICE
CERTIFICATE OF CORRECTION

PATENT NO. : 10,251,604 B2
APPLICATION NO. : 15/026888
DATED : April 9, 2019
INVENTOR(S) : Jonathan Coleman, Conor Boland and Umar Khan It is certified that error appears in the above-identified patent and that said Letters Patent is hereby corrected as shown below:

In the Claims

Claim 1, Column 17, Line 2: Please delete "deionized" and insert -- deionised --

Claim 1, Column 17, Line 3: Please delete "composite" and insert -- conductive --

Claim 7, Column 17, Line 40: Please delete "form" and insert -- from --

Claim 8, Column 17, Line 51: Please delete "[H]" and insert -- , --

Claim 12, Column 18, Line 38: Please delete "deionized" and insert -- deionised --

Claim 12, Column 18, Line 39: Please delete "composite" and insert -- conductive --

Claim 13, Column 18, Line 64: Please delete "step (a)" and insert -- step (i) --

Claim 13, Column 19, Line 10: Please delete "deionized" and insert -- deionised --

Claim 13, Column 19, Line 11: Please delete "composite" and insert -- conductive --

Claim 14, Column 19, Line 23: Please delete "sensitized" and insert -- sensitised --

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*